US010251830B2

(12) United States Patent
Nodari et al.

(10) Patent No.: US 10,251,830 B2
(45) Date of Patent: Apr. 9, 2019

(54) OXIDIZING COMPOSITION FOR TREATING KERATIN FIBRES, COMPRISING A PHOSPHORIC ACID MINERAL SALT, AND PROCESSES THEREFOR

(71) Applicant: L'OREAL, Paris (FR)

(72) Inventors: Laurent Nodari, Argenteuil (FR); Gautier Deconinck, Saint Gratien (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/366,875

(22) PCT Filed: Dec. 12, 2012

(86) PCT No.: PCT/EP2012/075153
§ 371 (c)(1),
(2) Date: Jun. 19, 2014

(87) PCT Pub. No.: WO2013/092323
PCT Pub. Date: Jun. 27, 2013

(65) Prior Publication Data
US 2014/0341826 A1 Nov. 20, 2014

Related U.S. Application Data

(60) Provisional application No. 61/610,588, filed on Mar. 14, 2012.

(30) Foreign Application Priority Data

Dec. 21, 2011 (FR) ..................... 11 62157

(51) Int. Cl.
| *A61K 8/92* | (2006.01) |
| *A61K 8/34* | (2006.01) |
| *A61Q 5/04* | (2006.01) |
| *A61Q 5/10* | (2006.01) |
| *A61K 8/22* | (2006.01) |
| *A61K 8/24* | (2006.01) |
| *A61K 8/31* | (2006.01) |
| *A61Q 5/08* | (2006.01) |
| *A45D 7/04* | (2006.01) |
| *A45D 7/00* | (2006.01) |

(52) U.S. Cl.
CPC .................. *A61K 8/92* (2013.01); *A45D 7/04* (2013.01); *A61K 8/22* (2013.01); *A61K 8/24* (2013.01); *A61K 8/31* (2013.01); *A61K 8/342* (2013.01); *A61Q 5/04* (2013.01); *A61Q 5/08* (2013.01); *A61Q 5/10* (2013.01); *A45D 2007/001* (2013.01)

(58) Field of Classification Search
None
See application file for complete search history.

(56) References Cited

U.S. PATENT DOCUMENTS

| 4,003,699 | A | 1/1977 | Rose et al. |
| RE30,199 | E | 1/1980 | Rose et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,766,576 | A | 6/1998 | Lowe et al. |
| 6,099,592 | A | 8/2000 | Vidal et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,730,789 | B1 | 5/2004 | Birault et al. |
| 7,862,803 | B2 * | 1/2011 | Kravtchenko ....... A61K 8/8158 424/401 |
| 8,262,739 | B2 | 9/2012 | Hercouet et al. |
| 8,343,238 | B1 * | 1/2013 | Lopez .................... A61Q 5/10 132/202 |
| 2002/0050013 | A1 | 5/2002 | Vidal et al. |
| 2003/0019051 | A9 | 1/2003 | Vidal et al. |
| 2003/0151024 | A1 | 8/2003 | Wegner |
| 2004/0141930 | A1 | 7/2004 | Legrand |
| 2006/0009371 | A1 | 1/2006 | Wang et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

International Search Report for PCT/EP2012/075153.
Todd, Charles, et al., "Volatile Silicone Fluids for Cosmetic Formulations," Cosmetics and Toiletries, vol. 91, Jan. 1976, pp. 29-32.
Porter, M.R., "Handbook of Surfactants," Blackie & Son, Ltd., 1991, pp. 117-178.
English language abstract for EP 0770375, dated Jul. 25, 2013.
English language abstract for FR 2683999, dated May 19, 2014.
English language abstract for FR 2886136, dated Apr. 23, 2014.
English language abstract for JP 2-19576, dated Jul. 18, 2012.
English language abstract for JP 5-163124, dated Jul. 18, 2012.

(Continued)

*Primary Examiner* — Jeffrey T. Palenik
(74) *Attorney, Agent, or Firm* — The Marbury Law Group, PLLC

(57) ABSTRACT

The present invention relates to an aqueous oxidizing composition for treating keratin fibers, comprising: —at least one oxidizing agent; —at least 40% by weight of at least one oil; —at least one phosphoric acid mineral salt; —the pH of the oxidizing composition being less than or equal to 5. The composition in accordance with the invention may be used for dyeing, bleaching or permanently reshaping keratin fibers. It produces ready-to-use compositions that give good dyeing, bleaching or permanent reshaping properties without degrading the keratin fibers and without impairing their cosmetic properties. Furthermore, the composition in accordance with the invention shows good stability over time, especially to storage at high temperatures, for example of about 45° C.

19 Claims, No Drawings

(56) References Cited

U.S. PATENT DOCUMENTS

| | | |
|---|---|---|
| 2009/0202598 A1 | 8/2009 | Kravtchenko et al. |
| 2010/0158844 A1 | 6/2010 | Braida-Valerio et al. |
| 2010/0178264 A1* | 7/2010 | Hercouet .................. A61K 8/19 |
| | | 424/62 |
| 2011/0232667 A1 | 9/2011 | Hercouet et al. |

FOREIGN PATENT DOCUMENTS

| | | |
|---|---|---|
| DE | 4133957 A1 | 4/1993 |
| DE | 19543988 A1 | 5/1997 |
| EP | 0770375 A1 | 5/1997 |
| EP | 1415641 A1 | 5/2004 |
| EP | 1728500 A1 | 12/2006 |
| FR | 2683999 A1 | 5/1993 |
| FR | 2733749 | 11/1996 |
| FR | 2801308 | 5/2001 |
| FR | 2885045 A1 | 11/2006 |
| FR | 2886136 A1 | 12/2006 |
| FR | 2940090 A1 | 6/2010 |
| GB | 1026978 | 4/1966 |
| GB | 1153196 | 5/1969 |
| JP | 219576 | 1/1990 |
| JP | 5163124 | 6/1993 |
| WO | 9408969 A1 | 4/1994 |
| WO | 9408970 A1 | 4/1994 |
| WO | 9615765 A1 | 5/1996 |
| WO | 2010070243 A1 | 6/2010 |

* cited by examiner

OXIDIZING COMPOSITION FOR TREATING KERATIN FIBRES, COMPRISING A PHOSPHORIC ACID MINERAL SALT, AND PROCESSES THEREFOR

This is a national stage application of PCT/EP2012/075153, filed internationally on Dec. 12, 2012, which claims priority to U.S. Provisional Application No. 61/610,588, filed on Mar. 14, 2012, as well as French Application No. 1162157, filed Dec. 21, 2011, all of which are incorporated herein by reference in their entireties.

The present invention relates to an aqueous oxidizing composition for treating keratin fibres, and in particular human keratin fibres such as the hair, comprising at least one oxidizing agent, at least one phosphoric acid mineral salt and at least 40% oil; the pH of the composition being less than or equal to 5.

In cosmetics, oxidizing compositions are used in the fields of dyeing, bleaching and permanently reshaping keratin fibres, and in particular human keratin fibres such as the hair.

Thus, in the oxidation dyeing of hair, oxidizing compositions are mixed with oxidation dyes (bases and couplers), which are intrinsically colourless, to generate coloured and colouring compounds via a process of oxidative condensation. Oxidizing compositions are also used in the direct dyeing of the hair as a mixture with certain direct dyes, which are coloured and colouring substances, in order to obtain coloration with a lightening effect on the hair. Among the oxidizing agents conventionally used for dyeing keratin fibres, mention may be made of hydrogen peroxide or compounds capable of producing hydrogen peroxide by hydrolysis, such as urea peroxide. Persalts such as perborates and persulfates may also be used. Hydrogen peroxide is more particularly preferred.

In hair bleaching, the compositions used contain one or more oxidizing agents. Among these agents, the ones most conventionally used are hydrogen peroxide or compounds that are capable of producing hydrogen peroxide by hydrolysis, such as urea peroxide or persalts such as perborates, percarbonates and persulfates, hydrogen peroxide and persulfates being particularly preferred.

These compositions may be aqueous compositions containing alkaline agents (amines or aqueous ammonia) that are mixed at the time of use with an aqueous hydrogen peroxide composition.

These compositions may also be formed from anhydrous products that contain alkaline compounds (amines and/or alkaline silicates), and a peroxygenated reagent such as ammonium or alkali metal persulfates, perborates or percarbonates, which is diluted at the time of use with an aqueous hydrogen peroxide composition.

In the permanent reshaping of the hair, in a first stage, the —S—S— disulfide bonds of keratin (cystine) are opened using a composition containing a suitable reducing agent (reduction step), and then, after having rinsed the head of hair thus treated, the said disulfide bonds are reconstituted, in a second stage, by applying to the hair, which has been placed under tension beforehand (rollers or the like), an oxidizing composition (oxidation step, also known as the fixing step) so as finally to give the hair the desired shape. This technique thus makes it possible, without preference, either to make the hair wavy or to relax or uncurl it. The new shape given to the hair by a chemical treatment such as that above is eminently long-lasting and especially withstands washing with water or shampoos, as opposed to the simple standard techniques of temporary reshaping, such as hair-setting.

The oxidizing compositions required for performing the fixing step are usually compositions based on aqueous hydrogen peroxide solution.

The oxidizing compositions that may be used may be in the form of aqueous solutions or emulsions.

For oxidizing compositions comprising large contents of oil and stabilized at pH values of 2, it has been found that the pH had a tendency to increase over time, during storage, which led to destabilization of the composition and thus to a loss of efficacy of the oxidizing agent.

The aim of the present invention is to provide novel oxidizing compositions that have improved stability on storage when compared with the existing oxidizing compositions, and which are thus more efficient.

This aim is achieved by the present invention, one subject of which is an aqueous composition for treating keratin fibres, in particular human keratin fibres such as the hair, comprising:
 at least one oxidizing agent;
 at least 40% by weight of at least one oil;
 at least one phosphoric acid mineral salt;
 the pH of the composition being less than or equal to 5.

When the composition is used in combination with a dye composition, good dyeing properties are obtained, especially strong, chromatic and sparingly selective colorations that show good resistance to the various attacking factors to which the hair may be subjected, such as shampoo, light, sweat and permanent reshaping operations, without impairing the cosmetic properties of the keratin fibres.

When the composition in accordance with the present invention is used for bleaching, it produces a good lightening effect on these fibres without degrading them and without impairing their cosmetic properties.

When the composition in accordance with the present invention is used for permanently reshaping keratin fibres, it produces satisfactory permanent reshaping of these fibres without degrading them and without impairing their cosmetic properties.

Thus, the composition in accordance with the invention shows good stability over time, especially to storage at high temperatures, for example of about 45° C.

A subject of the invention is also a process for treating keratin fibres, especially a process for dyeing, bleaching or permanently reshaping keratin fibres, using this oxidizing composition.

In the text hereinbelow, and unless otherwise indicated, the limits of a range of values are included in that range.

The human keratinous fibres treated by the method according to the invention are preferably the hair.

The expression "at least one" is equivalent to the expression "one or more".

The Oils

The term "oil" means a "fatty substance" that is liquid at room temperature (25° C.) and at atmospheric pressure (760 mmHg).

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They exhibit, in their structure, at least one hydrocarbon chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane. These fatty substances are neither polyoxyethylenated nor polyglycerolated.

In particular, the oils are chosen from $C_6$-$C_{16}$ lower alkanes; non-silicone oils of animal origin; glycerides of plant or synthetic origin; linear or branched hydrocarbons of mineral or synthetic origin, bearing more than 16 carbon atoms; fluoro oils; liquid fatty alcohols; liquid fatty esters; non-salified liquid fatty acids; silicone oils; or mixtures thereof.

The term "non-silicone oil" means an oil not containing any silicon atoms (Si) and the term "silicone oil" means an oil containing at least one silicon atom.

As regards the lower alkanes, these alkanes comprise from 6 to 16 carbon atoms and are linear or branched, optionally cyclic. Examples that may be mentioned include hexane, dodecane and isoparaffins such as isohexadecane and isodecane.

An example of a non-silicone oil of animal origin that may be mentioned is perhydrosqualene.

Glycerides of plant or synthetic origin that may be mentioned include liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

As regards the linear or branched hydrocarbons of mineral or synthetic origin, containing more than 16 carbon atoms, mention may be made most particularly of volatile or non-volatile liquid paraffins, and derivatives thereof, petroleum jelly, liquid petroleum jelly, polydecenes, and hydrogenated polyisobutene such as Parleam®.

The fluoro oils may be chosen especially from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols that are suitable for use in the invention are chosen more particularly from unsaturated or branched alcohols comprising from 8 to 30 carbon atoms. Examples that may be mentioned include 2-octyldodecan-1-ol, 2-butyloctanol, 2-hexyldecanol, 2-undecylpentadecanol, oleyl alcohol and linoleyl alcohol.

The fatty acids that may be used in the context of the invention are more particularly chosen from unsaturated or branched carboxylic acids comprising from 6 to 30 carbon atoms and in particular from 9 to 30 carbon atoms. They are advantageously chosen from oleic acid, linoleic acid, linolenic acid and isostearic acid. They must be non-salified, i.e. if they are present, the composition must not contain any mineral or organic basifying agents such as sodium hydroxide, potassium hydroxide, monoethanolamine or triethanolamine.

As regards the esters of a fatty acid and/or of a fatty alcohol, different from the glycerides mentioned above, mention may be made especially of liquid esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or unconjugated carbon-carbon double bonds.

The esters according to this variant may also be chosen from mono-, di-, tri- and tetraesters, and polyesters, and mixtures thereof.

These esters may be chosen, for example, from oleates, laurates, palmitates, myristates, behenates, cocoates, stearates, linoleates, linolenates, caprates and arachidonates, or mixtures thereof, such as, in particular, oleopalmitate, oleostearate or palmitostearate mixed esters.

More particularly, use is made of monoesters and diesters and in particular of sucrose, glucose or methylglucose mono- or dioleates, stearates, behenates, oleopalmitates, linoleates, linolenates or oleostearates.

An example that may be mentioned is the product sold under the name Glucate® DO by the company Amerchol, which is a methylglucose dioleate.

Among the sugar esters, it is also possible to use pentaerythrityl esters, preferably pentaerythrityl tetraisostearate, pentaerythrityl tetraoctanoate, and caprylic and capric hexaesters as a mixture with dipentaerythritol.

The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMSs), and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Organopolysiloxanes are defined in greater detail in Walter Noll's "Chemistry and Technology of Silicones" (1968), Academic Press. They can be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide or Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Volatile Silicone® FZ 3109, sold by Union Carbide, of formula:

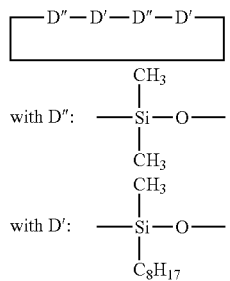

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) volatile linear polydialkylsiloxanes having from 2 to 9 silicon atoms and exhibiting a viscosity of less than or equal to $5 \times 10^{-6}$ m$^2$/s at 25° C. An example is decamethyltetrasiloxane, sold in particular under the name SH 200 by Toray Silicone. Silicones coming within this category are also described in the paper published in Cosmetics and Toiletries, Vol. 91, January 76, pp. 27-32, Todd & Byers *Volatile Silicone Fluids for Cosmetics*. The viscosity of the silicones is measured at 25° C. according to Standard ASTM 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from Dow Corning, such as DC200 having a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Among the silicones containing aryl groups are polydiarylsiloxanes, especially polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

According to one preferred variant, the oil(s) are chosen from $C_6$-$C_{16}$ lower alkanes; glycerides of plant or synthetic origin; linear or branched hydrocarbons of mineral or synthetic origin containing more than 16 carbon atoms; liquid fatty alcohols; liquid fatty esters; or mixtures thereof.

Even more preferentially, the oil(s) are chosen from $C_6$-$C_{16}$ lower alkanes; linear or branched hydrocarbons of mineral or synthetic origin containing more than 16 carbon atoms; liquid fatty alcohols; or mixtures thereof.

Preferably, the oil(s) are chosen from liquid petroleum jelly, isostearyl alcohol and octyldodecanol, or mixtures thereof.

The content of oil(s) advantageously ranges from 40% to 90% by weight, preferably from 45% to 80% by weight and better still from 50% to 70% by weight relative to the total weight of the composition.

Phosphoric Acid Mineral Salts

The phosphoric acid mineral salt(s) according to the invention are more particularly chosen from the compounds of formula (A) below:

in which x=1, 2 or 3

M=alkali metal, alkaline-earth metal, ammonium.

The phosphoric acid mineral salt(s) according to the invention may be in the form of solvate(s), especially hydrate(s).

Preferably, the phosphoric acid mineral salt(s) according to the invention are more particularly chosen from the compounds of formula (A) in which x=1.

Among these compounds, mention may be made of monosodium phosphate, monopotassium phosphate and monoammonium phosphate, optionally in the form of hydrate(s).

More particularly, the total content of phosphoric acid mineral salt or mixture thereof represents from 0.01% to 30% by weight relative to the weight of the composition, more particularly from 0.1% to 20% by weight and preferably from 1% to 10% by weight relative to the total weight of the composition.

Oxidizing Agents

The oxidizing agent(s) are more particularly chemical oxidizing agents (as opposed to compositions in which the only oxidizing agent is atmospheric oxygen) and may be chosen from hydrogen peroxide, peroxygenated salts, for instance alkali metal or alkaline-earth metal persulfates, percarbonates and perborates, urea peroxide, polythionates, alkali metal bromates or ferricyanides, and peracids, and precursors thereof, or mixtures thereof. Hydrogen peroxide is preferred.

The oxidizing agent(s) generally represent from 0.1% to 50% by weight and preferably from 1% to 20% by weight relative to the total weight of the composition according to the invention.

According to one particular embodiment of the invention, when the oxidizing agent is hydrogen peroxide, the oxidizing composition comprises one or more hydrogen peroxide stabilizers.

Examples of hydrogen peroxide stabilizers that may be mentioned in particular include alkali metal or alkaline-earth metal pyrophosphates, such as tetrasodium pyrophosphate, alkali metal or alkaline-earth metal stannates, phenacetin or oxyquinoline acid salts, for instance oxyquinoline sulfate. Preferably, one or more stannates are used optionally in combination with one or more pyrophosphates.

The hydrogen peroxide stabilizer(s) generally represent from 0.0001% to 5% by weight and preferably from 0.01% to 2% by weight relative to the total weight of the oxidizing composition.

According to one particular embodiment, the composition in accordance with the invention does not comprise any colorant or any persalt (peroxygenated salt).

The composition according to the present invention is aqueous.

It generally comprises from 5% to 59.5% by weight, better still from 20% to 58% by weight and even better still from 30% to 54% by weight of water relative to the total weight of the composition.

It may optionally comprise one or more water-soluble organic solvents. Examples of water-soluble organic solvents that may be mentioned include $C_1$-$C_4$ lower alkanols, such as ethanol and isopropanol; aromatic alcohols such as benzyl alcohol or phenoxyethanol; polyols or polyol ethers such as ethylene glycol monomethyl, monoethyl and monobutyl ether, propylene glycol or ethers thereof such as propylene glycol monomethyl ether, butylene glycol, dipropylene glycol, and also diethylene glycol alkyl ethers, for instance diethylene glycol monoethyl ether or monobutyl ether, or alternatively glycerol; and also mixtures thereof.

The water-soluble organic solvents are preferably present in proportions of between 0.1% and 35% by weight approximately and even more preferentially between 1% and 40% by weight approximately relative to the total weight of the oxidizing composition.

The pH of the oxidizing composition according to the invention is less than or equal to 5 and more particularly ranges from 1.5 to 4.5 and preferably from 2 to 3.5.

The pH of the composition according to the invention may be adjusted using acidifying agents, for instance phosphoric acid, hydrochloric acid, acetic acid, lactic acid, boric acid or citric acid.

Preferably, the pH of the composition according to the invention is adjusted using phosphoric acid.

The composition in accordance with the present invention may also comprise additional compounds conventionally used in cosmetics. These compounds may especially be chosen from thickening or stabilizing polymers, non-silicone conditioning polymers, non-liquid silicones, chelating agents, nonionic, anionic, cationic or amphoteric surfactants, and fragrances.

Preferably, the composition of the invention comprises at least one surfactant.

In particular, the surfactant(s) are chosen from anionic, amphoteric, zwitterionic, cationic and nonionic surfactants, and preferentially nonionic surfactants.

Examples of nonionic surfactants that may be used in the composition used according to the invention are described, for example, in the *Handbook of Surfactants* by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated or polyglycerolated, and containing at least one fatty chain comprising, for example, from 8 to 40 carbon atoms, it being possible for the number of ethylene oxide and/or propylene oxide groups to especially range from 2 to 200, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkyl glucamine and of N-acyl methylglucamine, aldobionamides, oxyethylenated and/or oxypropylenated silicones and amine oxides.

The nonionic surfactants are more particularly chosen from mono-oxyalkylenated or polyoxyalkylenated and monoglycerolated or polyglycerolated nonionic surfactants. The oxyalkylene units are more particularly oxyethylene or oxypropylene units, or their combination, preferably oxyethylene units.

Examples of oxyalkylenated nonionic surfactants that may be mentioned include:
oxyalkylenated ($C_8$-$C_{24}$)alkylphenols;
saturated or unsaturated and linear or branched oxyalkylenated $C_8$-$C_{30}$ alcohols;
saturated or unsaturated and linear or branched oxyalkylenated $C_8$-$C_{30}$ amides;
esters of saturated or unsaturated and linear or branched $C_8$-$C_{30}$ acids and of polyethylene glycols;
polyoxyethylenated esters of saturated or unsaturated and linear or branched $C_8$-$C_{30}$ acids and of sorbitol;
saturated or unsaturated oxyethylenated vegetable oils;
condensates of ethylene oxide and/or of propylene oxide, inter alia, alone or as mixtures;
oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with a preferred embodiment of the invention, the oxyalkylenated nonionic surfactants are chosen from oxyethylenated $C_8$-$C_{30}$ alcohols comprising from 1 to 100 mol of ethylene oxide; and polyoxyethylenated esters of saturated or unsaturated and linear or branched $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

Examples of compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the mono- or polyglycerolated alcohols, it is more particularly preferred to use the $C_8$/$C_{10}$ alcohol comprising 1 mol of glycerol, the $C_{10}$/$C_{12}$ alcohol comprising 1 mol of glycerol and the $C_{12}$ alcohol comprising 1.5 mol of glycerol.

Preferably, the surfactant(s) used in the composition of the invention are chosen from nonionic monooxyalkylenated or polyoxyalkylenated surfactants, more particularly monooxyethylenated or polyoxyethylenated, or monooxypropylenated or polyoxypropylenated, nonionic surfactants, or a combination thereof, more particularly monooxyethylenated or polyoxyethylenated.

More preferably still, the nonionic surfactants are chosen from polyoxyethylenated sorbitol esters and polyoxyethylenated fatty alcohols, and mixtures thereof.

In the composition of the invention, the amount of surfactant(s) in the composition preferably ranges from 0.1% to 50% by weight and better still from 0.5% to 20% by weight relative to the total weight of the composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of a cream, a gel, a milk, a lotion or a mousse, or in any other form that is suitable for treating keratin fibres, and especially human keratin fibres such as the hair. Preferably, it is in the form of a cream or a milk.

Fibre Treatment Process

Another subject of the invention is a process for treating keratin fibres, comprising the application to the keratin fibres of an oxidizing composition as defined previously.

The oxidizing composition in accordance with the invention may be used, for example, in a process for dyeing keratin fibres, and in particular human keratin fibres such as the hair.

The process for dyeing keratin fibres in accordance with the invention uses a dye composition comprising, in a support suitable for dyeing keratin fibres, one or more direct dyes and/or one or more oxidation dyes and an oxidizing composition as defined above.

According to this process, the dye composition is applied to the keratin fibres, the colour being revealed using an oxidizing composition according to the invention that is applied simultaneously or sequentially, with or without intermediate rinsing.

According to a particularly preferred embodiment of the dyeing process according to the invention, the dye composition is mixed, at the time of use, with an oxidizing composition according to the invention. The mixture obtained is then applied to the keratin fibres.

In general, the composition is left on the fibres for 3 to 50 minutes approximately and preferably 5 to 30 minutes approximately, after which the fibres are optionally washed with shampoo, rinsed again if necessary, and dried or left to dry.

The dye composition comprises at least one dye, chosen from oxidation dyes (bases/couplers) and direct dyes, or mixtures thereof.

The oxidation bases may be chosen from heterocyclic bases and benzenic bases, and mixtures thereof.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis((β-hydroxyethyl)-para-phenylenediamine, 4-N,N-bis((β-hydroxyethyl)amino-2-methylaniline, 4-N,N-bis((β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-((β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

Among these couplers, mention may be made especially of meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(6-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that can be used within the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.0001% to 10% by weight relative to the total weight of the composition, and preferably from 0.005% to 5% by weight relative to the total weight of the composition.

The coupler(s) each advantageously represent from 0.0001% to 10% by weight relative to the total weight of the composition, and preferably from 0.005% to 5% by weight relative to the total weight of the composition.

The direct dyes may themselves be synthetic or natural dyes, chosen from ionic or nonionic species, preferably cationic or nonionic species.

Examples of suitable synthetic direct dyes that may be mentioned include azo direct dyes; (poly)methine dyes such as cyanins, hemicyanins and styryls; carbonyl dyes; azine dyes; nitro(hetero)aryl dyes; tri(hetero)arylmethane dyes; porphyrin dyes; and phthalocyanin dyes, alone or as mixtures.

Mention may be made, among the natural direct dyes which can be used according to the invention, of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

When they are present, the direct dye(s) more particularly represent from 0.001% to 10% by weight and preferably from 0.005% to 5% by weight of the total weight of the composition.

The oxidizing composition according to the invention may also be used in a process for bleaching keratin fibres, and in particular human keratin fibres such as the hair.

The bleaching process according to the invention comprises a step of applying to the keratin fibres a bleaching composition preferably comprising aqueous hydrogen peroxide solution, after extemporaneous mixing.

The bleaching composition applied to the keratin fibres may be obtained by mixing, at the time of use, an oxidizing composition according to the invention with an aqueous or anhydrous composition preferably containing one or more alkaline agents. The anhydrous composition may be pulverulent or in paste form, and in both cases preferably contains one or more peroxygenated salts, in particular one or more persulfates. The anhydrous composition in paste form also contains one or more inert organic liquids.

In general, the leave-on time of the composition on the fibres ranges from 1 to 60 minutes approximately and preferably from 1 to 30 minutes approximately.

Usually, the temperature at which the composition is applied is from about 15 to 80° C. and preferably from 15 to 40° C.

Once the desired bleaching has been obtained, the bleaching mixture is usually removed by rinsing the fibres with water, preferably followed by washing them at least once with a shampoo, and then optionally drying them.

Another subject of the present invention is a process for permanently reshaping keratin fibres, and in particular human keratin fibres such as the hair, using an oxidizing composition as defined above.

According to this process, a reducing composition is applied to the keratin fibres to be treated, the keratin fibres being placed under mechanical tension before, during or after the application of the reducing composition, the fibres are optionally rinsed, the oxidizing composition of the present invention is applied to the optionally rinsed fibres, and the fibres are then once again optionally rinsed.

The first step of this process consists in applying a reducing composition to the hair. This application is performed lock by lock or all at once.

The reducing composition comprises at least one reducing agent, which may be chosen in particular from thioglycolic acid, cysteine, cysteamine, glyceryl thioglycolate, thiolactic acid, or thiolactic or thioglycolic acid salts.

The usual step for placing the hair under tension in a shape corresponding to the final shape desired for this hair (for example curls) may be performed by any means, especially mechanical means, which is suitable and known per se for holding the hair under tension, for instance rollers, curlers, combs and the like.

The hair may also be shaped without the aid of external means, simply with the fingers.

Before performing the next optional rinsing step, the head of hair onto which the reducing composition has been applied should conventionally be left to stand for a few minutes, generally between 5 minutes and 1 hour and preferably between 10 and 30 minutes, so as to give the reducing agent enough time to act correctly on the hair. This waiting phase preferably takes place at a temperature ranging from 35° C. to 45° C., while preferably also protecting the hair with a bonnet.

In the second optional rinsing step, the hair impregnated with the reducing composition is rinsed thoroughly with an aqueous composition.

Next, in a third step, the oxidizing composition according to the present invention is applied to the hair thus rinsed, with the aim of fixing the new shape given to the hair.

As in the case of the application of the reducing composition, the head of hair onto which the oxidizing composition has been applied is then, conventionally, left in a standing or waiting phase that lasts a few minutes, generally between 3 and 30 minutes and preferably between 5 and 15 minutes.

If the tension of the hair is maintained by external means, these means (rollers, curlers and the like) may be removed from the head of hair before or after the fixing step.

Lastly, in the final step of the process according to the invention, which is also an optional step, the hair impregnated with the oxidizing composition is rinsed thoroughly, generally with water.

A subject of the present invention is also the use for treating keratin fibres, and in particular human keratin fibres such as the hair, of an oxidizing composition as defined above.

A subject of the present invention is especially the use for treating keratin fibres, and in particular human keratin fibres such as the hair, of an oxidizing composition as defined above.

A subject of the present invention is also the use for bleaching keratin fibres, and in particular human keratin fibres such as the hair, of an oxidizing composition as defined above.

A subject of the present invention is also the use for permanently reshaping keratin fibres, and in particular human keratin fibres such as the hair, of an oxidizing composition as defined above.

The examples that follow illustrate the invention without, however, being limiting in nature.

EXAMPLE

The following composition is prepared (amounts in g %):

| | |
|---|---|
| Cetylstearyl alcohol (30/70 C16/C18) | 6 |
| Oxyethylenated stearyl alcohol (20 OE) | 6 |
| Liquid petroleum jelly | 50 |
| Protected oxyethylenated rapeseed acid amide (4 OE) | 1.6 |
| Vitamin E: DL-α-Tocopherol | 0.1 |
| Glycerol | 0.5 |
| Tetrasodium pyrophosphate decahydrate | 0.05 |

| | |
|---|---|
| 50% hydrogen peroxide solution (200 vol. aqueous hydrogen peroxide solution) | 18 |
| Etidronic acid, tetrasodium salt, as a 30% aqueous solution | 0.2 |
| Sodium salicylate | 0.04 |
| Monosodium phosphate dihydrate | 2 |
| Phosphoric acid | qs pH = 2 |
| deionized water | qs 100 |

After storage for two months at 45° C., the composition is stable, and in particular its pH has not changed.

The invention claimed is:

1. An aqueous oxidizing composition for treating keratin fibers, comprising:
   at least one oxidizing agent;
   at least 40% by weight of at least one oil; and
   at least one phosphoric acid mineral salt, present in an amount ranging from about 1% to about 10% by weight, relative to the total composition,
   wherein the pH of the oxidizing composition is less than or equal to 5, and
   wherein the at least one phosphoric acid mineral salt is chosen from the compounds of formula (A) and solvates thereof:

$$H_2PO_4M \quad (A)$$

wherein M is chosen from alkali metals, alkaline-earth metals, and ammonium.

2. The composition according to claim 1, wherein the at least one oil is chosen from $C_6$-$C_{16}$ lower alkanes; non-silicone oils of animal origin; glycerides of plant or synthetic origin; linear or branched hydrocarbons of mineral or synthetic origin comprising more than 16 carbon atoms; fluoro oils; liquid fatty alcohols; liquid fatty esters; non-salified liquid fatty acids; silicone oils; and mixtures thereof.

3. The composition according to claim 2, wherein the at least one oil is chosen from $C_6$-$C_{16}$ lower alkanes; linear or branched hydrocarbons of mineral or synthetic origin comprising more than 16 carbon atoms; liquid fatty alcohols; and mixtures thereof.

4. The composition according to claim 3, wherein the at least one oil is chosen from liquid petroleum jelly, isostearyl alcohol, octyldodecanol, and mixtures thereof.

5. The composition according to claim 1, wherein the content of the at least one oil is present in an amount ranging from about 40% to about 90% by weight, relative to the total weight of the composition.

6. The composition according to claim 5, wherein the at least one oil is present in an amount ranging from about 50% to about 70% by weight, relative to the total weight of the composition.

7. The composition according to claim 1, wherein the at least one phosphoric acid mineral salt is chosen from monosodium phosphate, monopotassium phosphate, monoammonium phosphate, combinations thereof, and hydrates thereof.

8. The composition according to claim 1, wherein the at least one oxidizing agent is chosen from hydrogen peroxide, persalts, urea peroxide, polythionates, alkali metal bromates, ferricyanides, peroxygenated salts, and mixtures thereof.

9. The composition according to claim 8, wherein the at least one oxidizing agent is chosen from alkali metal and alkaline earth metal persulfates, perborates, and percarbonates.

10. The composition according to claim 1, wherein the at least one oxidizing agent is present in an amount ranging from about 0.1% to about 50% by weight, relative to the total weight of the composition.

11. The composition according to claim 10, wherein the at least one oxidizing agent is present in an amount ranging from about 1% to about 20% by weight, relative to the total weight of the composition.

12. The composition according to claim 1, wherein the pH is adjusted using phosphoric acid.

13. The composition according to claim 1, further comprising at least one surfactant.

14. The composition according to claim 1, further comprising at least one hydrogen peroxide stabilizer chosen from alkali metal or alkaline-earth metal pyrophosphates, alkali metal or alkaline-earth metal stannates, phenacetin or oxyquinoline acid salts, and mixtures thereof.

15. The composition according to claim 1, wherein the at least one phosphoric acid mineral salt is chosen from monosodium phosphate, monopotassium phosphate, combinations thereof, and hydrates thereof.

16. A process for treating keratin fibers, comprising applying to the keratin fibers a composition according to claim 1.

17. A process for dyeing keratin fibers, comprising applying to the keratin fibers a composition according to claim 1.

18. A process for bleaching keratin fibers, comprising applying to the keratin fibers a composition according to claim 1.

19. A process for permanently reshaping keratin fibers, comprising applying to the keratin fibers a composition according to claim 1.

* * * * *